(12) United States Patent
De La Riva

(10) Patent No.: US 9,707,984 B2
(45) Date of Patent: Jul. 18, 2017

(54) METHOD AND DEVICE FOR INSPECTING RAILWAY WHEELS

(71) Applicant: HEGENSCHEIDT-MFD GMBH & CO. KG, Erkelenz (DE)

(72) Inventor: Camilo De La Riva, Grevenbroich (DE)

(73) Assignee: Hegenscheidt-MFD GmbH & Co. KG, Erkelenz (DE)

( * ) Notice: Subject to any disclaimer, the term of this patent is extended or adjusted under 35 U.S.C. 154(b) by 269 days.

(21) Appl. No.: 14/412,262

(22) PCT Filed: Jul. 2, 2013

(86) PCT No.: PCT/DE2013/000370
§ 371 (c)(1),
(2) Date: Apr. 23, 2015

(87) PCT Pub. No.: WO2014/005574
PCT Pub. Date: Jan. 9, 2014

(65) Prior Publication Data
US 2015/0239480 A1 Aug. 27, 2015

(30) Foreign Application Priority Data
Jul. 4, 2012 (DE) .......................... 10 2012 013 626

(51) Int. Cl.
G01N 27/82 (2006.01)
B61K 9/12 (2006.01)
G01M 17/10 (2006.01)

(52) U.S. Cl.
CPC ............... *B61K 9/12* (2013.01); *G01M 17/10* (2013.01); *G01N 27/82* (2013.01)

(58) Field of Classification Search
CPC .......... B61K 9/12; G01M 17/10; G01N 27/82
See application file for complete search history.

(56) References Cited

U.S. PATENT DOCUMENTS

| | | | |
|---|---|---|---|
| 1,702,997 A | 2/1929 | Ewing et al. | |
| 2,442,491 A | 6/1948 | Giesking et al. | |
| (Continued) | | | |

FOREIGN PATENT DOCUMENTS

| | | |
|---|---|---|
| DE | 4031899 A1 | 4/1992 |
| DE | 69303989 T2 | 1/1997 |
| (Continued) | | |

OTHER PUBLICATIONS

International Preliminary Report on Patentabilityfor PCT/DE2013/000370 with English Translation thereof, IB/Geneva, issued Jan. 6, 2015, incorporating the English Translation of the Written Opinion of the ISA, ISA/EP, Rijswijk, NL, mailed Feb. 3, 2014.

(Continued)

*Primary Examiner* — Daniel Miller
(74) *Attorney, Agent, or Firm* — Harness, Dickey & Pierce, P.L.C.

(57) ABSTRACT

The present invention concerns a method and a device for inspecting railway wheels with respect to use-related wear and/or a material defect. The task of the present invention is to create a technical solution in this regard by means of which various configurations of railway wheels can be tested in a short time. In particular, an inspection should be carried out in override mode so that the test results for a complete train can be prepared during the passage time over an allocated test device. This task is accomplished in that the rolling railway wheelset passes through a spatially restricted magnetic field that is coupled through the rails along which the allocated rail vehicle is guided. For this purpose, a device is used in which an electromagnet (4; 5) is arranged between the rails (2; 3) on which a measuring coil is also configured for registering changes in the magnetic flux.

11 Claims, 2 Drawing Sheets

(56) References Cited

U.S. PATENT DOCUMENTS

| | | | |
|---|---|---|---|
| 3,844,513 | A | 10/1974 | Bernhardson et al. |
| 5,363,702 | A | 11/1994 | Catot et al. |
| 6,262,573 | B1 | 7/2001 | Wojnarowski et al. |
| 6,523,411 | B1 | 2/2003 | Mian et al. |
| 2007/0043486 | A1 | 2/2007 | Moffett et al. |

FOREIGN PATENT DOCUMENTS

| | | | |
|---|---|---|---|
| DE | 19836513 | A1 | 2/2000 |
| DE | 19924781 | A1 | 11/2000 |
| DE | 19943744 | A1 | 3/2001 |
| DE | 10352166 | B3 | 3/2005 |
| DE | 112006002123 | T5 | 7/2008 |
| WO | WO-2009054566 | A1 | 4/2009 |

OTHER PUBLICATIONS

International Search Report for PCT/DE2013/000370, ISA/EP, Rijswijk, NL, mailed Feb. 3, 2014.

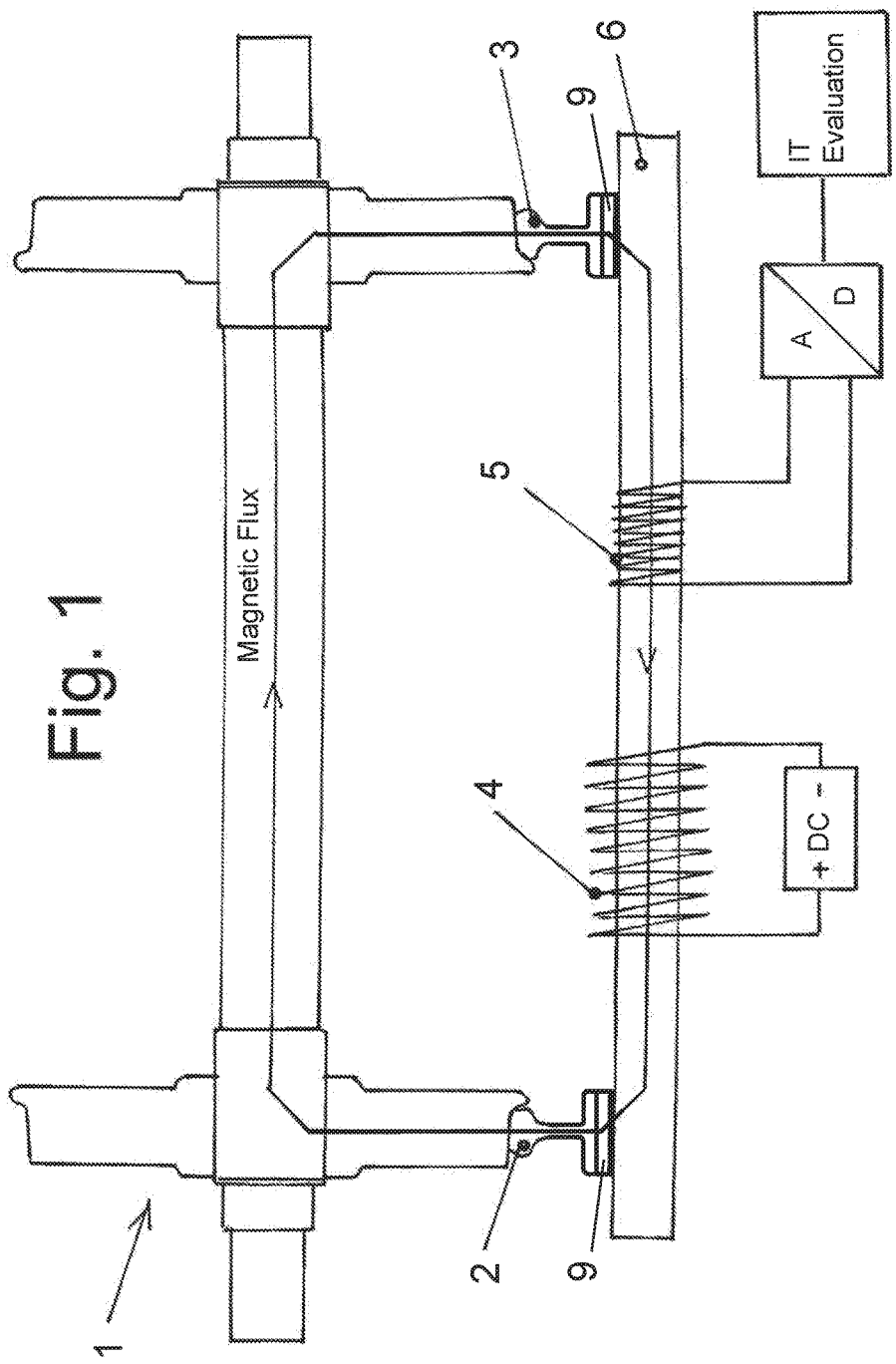

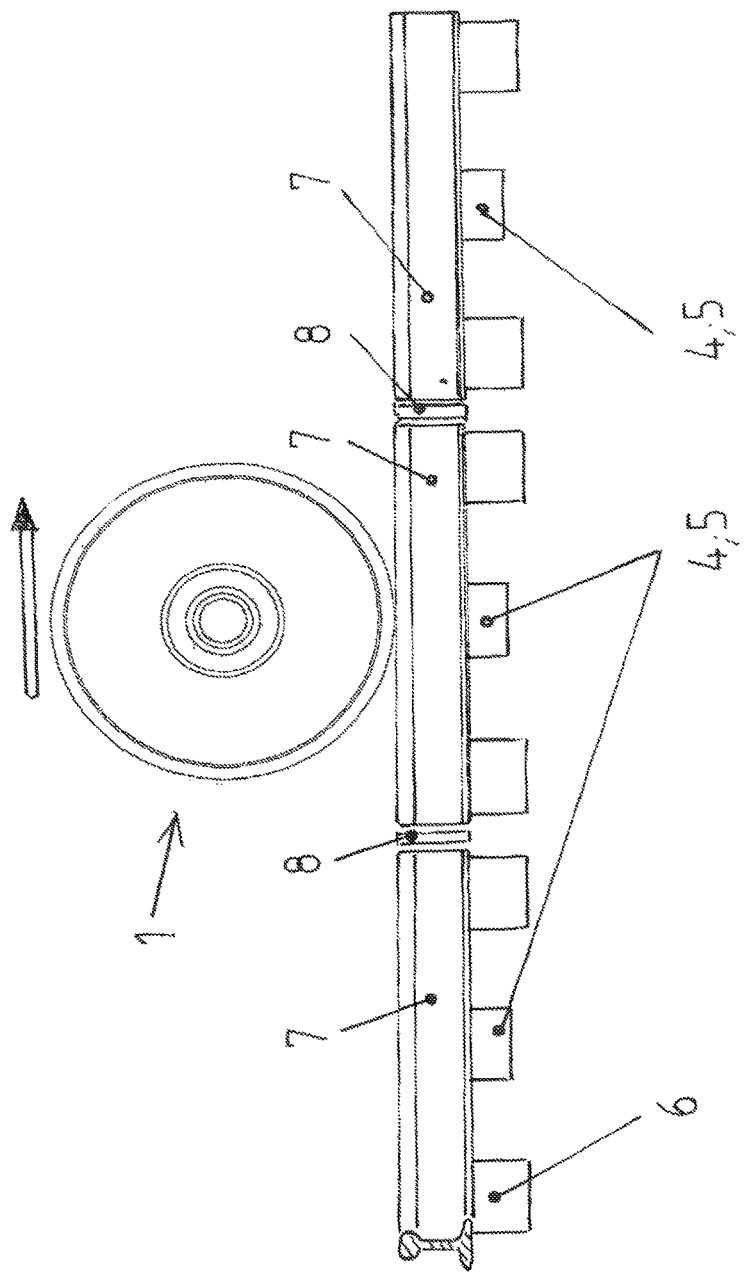

METHOD AND DEVICE FOR INSPECTING RAILWAY WHEELS

CROSS-REFERENCE TO RELATED APPLICATIONS

This application is a U.S. National Phase Application under 35 USC 371 of International Application No. PCT/DE2013/00370, filed Jul. 2, 2013 and published in German as WO 2014/005574 on Jan. 9, 2014. This application claims the benefit of German Patent Application No. 1020120136269, filed Jul. 4, 2012. The disclosures of the above applications are incorporated herein by reference.

FIELD

The present invention relates to a technical solution for inspecting railway wheels with respect to use-related wear and/or a material defect, in which the railway wheel installed in a railway vehicle is tested while this railway vehicle is in motion.

BACKGROUND AND SUMMARY

Railway wheels are known in different versions, for example with a wheel flange that rolls along the rail and is shrink-fitted onto a wheel body or with a wheel disc comprising solid material in which the running surface is configured as an integral part of this wheel disc. Irrespective of the specific version, railway wheels are components in the wheel/rail system which are exposed to high loadings and are subject to unavoidable wear as a result of their contact with the rail. The raceways undergo wear as a result of their contact with the rail head and the wheel track flanges undergo wear as a result of their contact with the inside surface of the rail head, especially on curved tracks and when passing through switches. In addition to this functionally related wear on the wheels, it is also possible for material defects to occur as a result of overloading the wheels or production errors during manufacture. As a result, railway wheels are regularly investigated for material defects either manually or semi-automatically with established methods (ultrasound, eddy currents, X-ray), so as to guarantee continued safe vehicle operation. A train incorporates a large number of wheelsets, however, meaning that inspections of this type entail lengthy downtimes and require highly qualified personnel, as well as calling for the extensive use of test technology. Various state-of-the-art test methods have already been disclosed in this regard.

For example, DE 693 03 989 T2 describes a technical solution that is, in a preferred embodiment, suitable for use by manufacturers of railway wheels in testing the hardness and residual stresses in railway wheels: The hardness test is carried out by ball indentation and the residual stress test by ultrasound, in which case a scaffold-like device is used which features numerous holding and displacement devices for handling the measuring technology.

DE 103 52 166 B3 concerns a device designed for use in the workshop for semiautomatically measuring the surface composition of the running surface of railway wheels in installed condition. In this case, a measuring device for each of the two wheels of a wheelset is arranged on a measuring platform. Once both wheels have been raised somewhat and set in rotation, the running surface of each wheel is scanned step-by-step by a measuring beam. The distances measured by the measuring beam between the measuring device and the running surface of the wheel are evaluated by computer technology in order to estimate out-of-roundness values and surface composition.

DE 11 2006 002 123 T5 discloses a device with a so-called gauge head that can be mounted on a railway wheel in a releasable connection and has several sensors assigned to it for measuring typical geometrical components of the railway wheel, for example a wheel flange height sensor and a wheel flange thickness sensor. This gauge head is in an active connection with a control and evaluation device.

DE 199 24 781 A1 describes a further technical solution for checking a railway wheel installed in a rail vehicle. In this case, a railway train is driven over a section of test track at low speed. A test probe is propelled by a linear drive on a guide rail parallel to the test track and is initially set to the travelling speed of the train, after which the test probe contacts the railway wheel.

A solution involving a similar approach is disclosed in DE 199 43 744 B4, in which case the wheel flange and the clamping edge are, in a preferred embodiment, tested simultaneously by means of several probes while the train is moving into a maintenance hall along a test track for routine inspections.

Although a large number of technical solutions have been disclosed for inspecting railway wheels, further development is nevertheless still required. This is due in particular to an ever-increasing demand for automated, robust and efficient test technology.

The task of the present invention is to create a technical solution by means of which various configurations of railway wheels and their components or component sections that are exposed to wear can be tested in a short time and at an acceptable cost in order to identify possible damage. In particular, the railway wheels should be inspected in override mode so that the test results for a complete train can be prepared during the passage time over an allocated test device. In addition, detection of various types of defect should be guaranteed during the test process, In terms of the procedure, this task is accomplished in that the rolling railway wheelset passes through a spatially restricted magnetic field that is coupled through the rails along which the allocated rail vehicle is guided. For this purpose, a device is used in which there is an electromagnet arranged between the rails, and on which a measuring coil is also configured for registering changes in the magnetic flux. Advantageous embodiments are dealt with in subordinate claims, the technical characteristics of which are explained in more detail in the design example.

In accordance with the present invention, the material test of railway wheels is carried out by analysing the magnetic flux that passes through a loaded, rolling wheelset. For this purpose, a track segment is prepared in such a way that a left and a right rail form the pole shoes of a magnet in terms of function. Railways wheels of the normal version consist of several components made of ferromagnetic steel, especially a wheelset shaft, two wheel discs as well as possibly also brake discs and/or drive gears. The magnetic flux through the wheel from one rail of the track to the other is modulated by the Hertzian contact surfaces of the wheel/rail, by the seats of the wheel discs on the shaft and by the so-called Barkhausen noise in the pre-magnetised and rotating material exposed to alternating loads. The modulations in a precisely rotationally symmetrical wheel body are different from those in a wheel body that has singularities in its structure or in the running surfaces. As a result, the signals differ depending on the current wheel condition. The corresponding signal profiles are analysed, classified and allocated to specific wheelset conditions according to their characteristics.

As a result, the present invention provides a technical solution for verifying material defects in installed railway wheels while a train is travelling, in which case the underlying approach to the solution involves troubleshooting in the rolling wheelset using magnetic flux changes.

DRAWINGS

The drawing shows a design example of the present invention. In the drawing,

FIG. 1 shows the basic structure of a device in accordance with the present invention, in a stylised cross-section FIG. 2 shows the device in accordance with FIG. 1 in a side view

DETAILED DESCRIPTION

The device shown in the drawing is designed for inspecting railway wheels that are installed in a rail vehicle (not shown). In this case, the wheelset 1 rolls along a track section during movement of the rail vehicle, with an electromagnet arranged between the left rail 2 and the right rail 3. The electromagnet comprises an exciter coil 4 and a detector coil 5 which acts as a measuring coil for registering changes in the magnetic flux.

The electromagnet 4; 5 consists, in a preferred embodiment, of transformer sheet metal or ferrite in order to keep eddy current losses low in the measuring signals. The electromagnet 4; 5 can be configured in various ways. In this way, the rails 2 and 3 can be connected by a threshold 6 that is functionally configured as an electromagnet on which a measuring coil 5 is configured in turn for registering changes in the magnetic flux. Alternatively, it is possible for the electromagnet 4; 5 to be installed between the rails 2 and 3 as a threshold without a carrying function. Irrespective of the specific version, Hall elements or functionally equivalent magnetic field sensors 9 are incorporated between the rails 2 and 3 and the electromagnet 4; 5 in order to register changes in the magnetic flux which take place quickly over time.

In a preferred embodiment, the length and the number of segments 7 in the track sections comprising two rails 2; 3 in each case are selected in such a way that at least two wheelsets 1 located close to one another (such as in a bogie) can be tested in parallel. In addition, it is advantageous if the length and number of these track segments 7 is selected in such a way that a complete rotation of a normal railway wheel can be tested with each segment 7. These requirements can be met if, for example, four track segments 7 with a length of 1.1 meter each are used, although this should not be evaluated as a restriction on the configuration in accordance with the present invention. In another advantageous embodiment, successive segments 7 are each separated from one another by MU-metal (permalloy) plates 8 and are fishplated together.

For inspecting railway wheels with respect to use-related wear and/or a material defect, the installed railway wheel is set in motion with the corresponding railway vehicle, with the rolling direction indicated by a stylised arrow in FIG. 2. With use of the device in accordance with FIG. 1 and FIG. 2, the rolling railway wheelset 1 passes through of spatially restricted magnetic field. The magnetic field is coupled by the rails 2 and 3 along which the allocated rail vehicle is guided. The magnetic flux is indicated in FIG. 1 with a circulating stylised arrow contour. This involves inducing measuring signals which are influenced in particular by the rolling contacts between the wheel and rail, by the wheel load and by the material structure in the wheelset 1. By evaluating these measuring signals, it is possible to make a statement about usage-related wear or other material defects in the tested railway wheelsets 1.

The invention claimed is:

1. A method for inspecting the wheels of a railway wheelset for use-related wear and/or a material defect, comprising:
    providing a pair of parallel rails extending along a length and which are connected to each other at discrete intervals along the length by a plurality of thresholds made from transformer sheet metal or ferrite, each threshold comprising an exciter coil and a detector coil;
    placing the railway wheelset in motion on the pair of rails;
    activating the exciter coil of each threshold and generating a spatially restricted magnetic field at each of the discrete intervals along the length of the rails;
    rolling the railway wheelset along the length of the rails so that it passes through each spatially restricted magnetic field;
    measuring a magnetic flux passing through the railway wheelset with the detector coil at each discrete location to determine a plurality of magnetic flux measurements; and
    analyzing any variations in the plurality of magnetic flux measurements to determine use-related wear and/or a material defect in the wheels of the railway wheelset.

2. A method according to claim 1, further comprising locating a magnetic field sensor between each rail and each threshold.

3. The method of claim 1, wherein measuring the magnetic flux passing through the railway wheelset comprises measuring a magnetic flux from the threshold to a first wheel disc of the railway wheelset through a wheelset shaft of the railway wheelset to a second wheel disc of the railway wheelset to the threshold.

4. The method of claim 3, wherein measuring a magnetic flux passing through the railway wheelset comprises registering changes in the magnetic flux at the detector coil.

5. A device for inspecting the wheels of a railway wheelset for use-related wear and/or a material defect, comprising:
    a pair of parallel rails extending along a length;
    a plurality of thresholds made from transformer sheet metal or ferrite being spaced apart at discrete intervals along the length of the rails, one threshold being disposed between and connected to each rail of the pair rails at each discrete interval, and each threshold comprising an exciter coil and a detector coil;
    wherein each threshold is operable to generate a spatially restricted magnetic field at each of the discrete intervals along the length of the rails when the exciter coil is activated; and
    wherein, when the railway wheelset is passed through each spatially restricted magnetic field, each detector coil is operable to measure a magnetic flux passing from the threshold to a first wheel disc of the railway wheelset through a wheelset shaft of the railway wheelset to a second wheel disc of the railway wheelset to the threshold.

6. The device according to claim 5, further comprising a magnetic field sensor positioned between each rail and each threshold located at each discrete interval.

7. The device according to claim 5, wherein the discrete intervals are spaced apart at a distance greater than a diameter of the first wheel disc of the railway wheelset.

8. The device according to claim 7, wherein the discrete intervals are spaced apart at a distance greater than a circumference of the first wheel disc of the railway wheelset.

9. The device according to claim 5 wherein each of the pair of rails is divided into a plurality of segments along the length, each segment being separated from an adjacent segment by a MU-metal plate and fishplated to the adjacent segment.

10. The device according to claim 9 wherein the number of segments equals the number of discrete intervals.

11. A device for inspecting the wheels of a railway wheelset for use-related wear and/or a material defect, comprising:
- a plurality of rail segments, each rail segment comprising a pair of parallel rails extending along a length;
- each rail segment of the plurality of rail segments being separated from an adjacent rail segment of the plurality of rail segments by a MU-metal plate;
- wherein the pair of parallel rails of each rail segment are connected by a threshold made from transformer sheet metal or ferrite;
- wherein each threshold comprises an exciter coil and a detector coil;
- a magnetic field sensor incorporated between at least one of the pair of parallel rails and at least one of the exciter coil and the detector coil of the threshold of each rail segment;
- wherein each threshold is operable to generate a spatially restricted magnetic field when the exciter coil is activated; and
- wherein each detector coil is operable to measure a magnetic flux passing from the threshold to a first wheel disc of the railway wheelset through a wheelset shaft of the railway wheelset to a second wheel disc of the railway wheelset to the threshold when the railway wheelset is passed through the spatially restricted magnetic field.

* * * * *

UNITED STATES PATENT AND TRADEMARK OFFICE
CERTIFICATE OF CORRECTION

PATENT NO. : 9,707,984 B2
APPLICATION NO. : 14/412262
DATED : July 18, 2017
INVENTOR(S) : Camilo De La Riva It is certified that error appears in the above-identified patent and that said Letters Patent is hereby corrected as shown below:

On the Title Page

In Column 2, Other Publications, the phrase "Patentabilityfor" should be replaced with --Patentability for--.

In the Claims

In Column 4, Claim 2, Line 33, the word "A" should be replaced with --The--.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*